US00PP37476P3

(12) United States Plant Patent
Yu et al.

(10) Patent No.: US PP37,476 P3
(45) Date of Patent: Jun. 16, 2026

(54) ***NELUMBO* PLANT NAMED 'SCAU Star'**

(50) Latin Name: *Nelumbo nucifera*
Varietal Denomination: SCAU Star

(71) Applicants: Huapin(Hainan) Agricultural Sci-Tech Co., Ltd., Sanya (CN); South China Agricultural University, Guangzhou (CN)

(72) Inventors: Shujun Yu, Guangzhou (CN); Ruobang Cen, Guangzhou (CN); Meifen Li, Guangzhou (CN); Qi Pan, Sanya (CN)

(73) Assignees: Southern China Agricultural University (CN); Lu'An Yugarden Horticulture Co., Ltd. (CN)

( * ) Notice: Subject to any disclaimer, the term of this patent is extended or adjusted under 35 U.S.C. 154(b) by 303 days.

(21) Appl. No.: 18/223,877

(22) Filed: Jul. 19, 2023

(65) Prior Publication Data
US 2025/0031591 P1 Jan. 23, 2025

(51) Int. Cl.
*A01H 5/02* (2018.01)
*A01H 6/00* (2018.01)

(52) U.S. Cl.
USPC ..... Plt./342
CPC ..... *A01H 6/00* (2018.05)

(58) Field of Classification Search
USPC ..... Plt./342
See application file for complete search history.

*Primary Examiner* — Susan McCormick Ewoldt

(57) ABSTRACT

A new and distinct cultivar of *Nelumbo* plant named 'SCAU STAR' is disclosed, characterized by double flowers having red petals and yellow centers. Petals have a visible vein pattern. The new variety is useful as both an ornamental plant and for cut flower production.

3 Drawing Sheets

Latin name of the genus and species: *Nelumbo nucifera*.
Variety denomination: 'SCAU STAR'.

BACKGROUND OF THE INVENTION

The new cultivar, *Nelumbo* 'SCAU Star', is the product of a planned breeding program. The new variety originated from an open-pollination of the unpatented seed parent variety 'Gudu Hongyun'. The pollen parent variety is unknown. The open-pollination was made during July of 2019 in Guangzhou, China at a research nursery. The new cultivar 'SCAU Star' was selected in July of 2020 at the same location.

Asexual reproduction of the new cultivar 'SCAU Star' was first performed by root division in Guangzhou, China at a research nursery in March of 2021. *Nelumbo* 'SCAU Star' has since produced multiple generations and has shown that the unique features of this cultivar are stable and reproduced true to type.

SUMMARY OF THE INVENTION

The cultivar 'SCAU Star' has not been observed under all possible environmental conditions. The phenotype may vary somewhat with variations in environment such as temperature, day length, and light intensity. without, however, any variance in genotype.

The following traits have been repeatedly observed and are determined to be the unique characteristics of 'SCAU Star'. These characteristics in combination distinguish 'SCAU Star' as a new and distinct *Nelumbo* cultivar:

1. Red petals.
2. Double flowers.

3. Visible vein pattern on petals.
4. Yellow flower centers.

PARENTAL COMPARISON

Plants of the new cultivar 'SCAU Star' are similar to plants of the seed parent in most horticultural characteristics. However, plants of the new cultivar 'SCAU Star' differ in the following:

1. Flower color of the new variety is red with a yellow center, while the flower color of the seed parent is solid red.
2. Flowers of the new variety have on average 40 to 45 petals; flowers of the seed parent have on average 15 petals.
3. Petal vein pattern of the new variety is not as fine as the petal vein pattern of the seed parent.

COMMERCIAL COMPARISON

The new cultivar 'SCAU Star' can be compared to the unpatented commercial variety *Nelumbo* 'Shicheng Huoba'. Plants of the new cultivar 'SCAU Star' differ in the following:

1. Petals of 'SCAU' are not as wide of petals of this comparator.
2. Petals of the new variety are darker red than petals of this comparator.
3. The vein pattern is more easily visible in the new variety.

The new cultivar 'SCAU Star' can be compared to the unpatented commercial variety *Nelumbo* 'Gudu Jingfang'. Plants of the new cultivar 'SCAU Star' differ in the following:

1. Petals of 'SCAU' are wider than of petals of this comparator.
2. Petals of the new variety are darker red without the purple tone found on petals of this comparator.
3. A petaloid stamen is present in the new variety; this comparator lacks this feature.

BRIEF DESCRIPTION OF THE PHOTOGRAPHS

The accompanying photographs illustrate in full color typical plants of 'SCAU Star' grown outdoors, in a pond, in Xuanwu district, Nanjing, China. The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Nelumbo* plant. Temperatures ranged from approximately 20° C. to 30° C. night and about 25° C. to 38° C. during the day. No artificial light, photoperiodic treatments or chemical treatments were given to the plants.

DETAILED BOTANICAL DESCRIPTION

Figure 1:
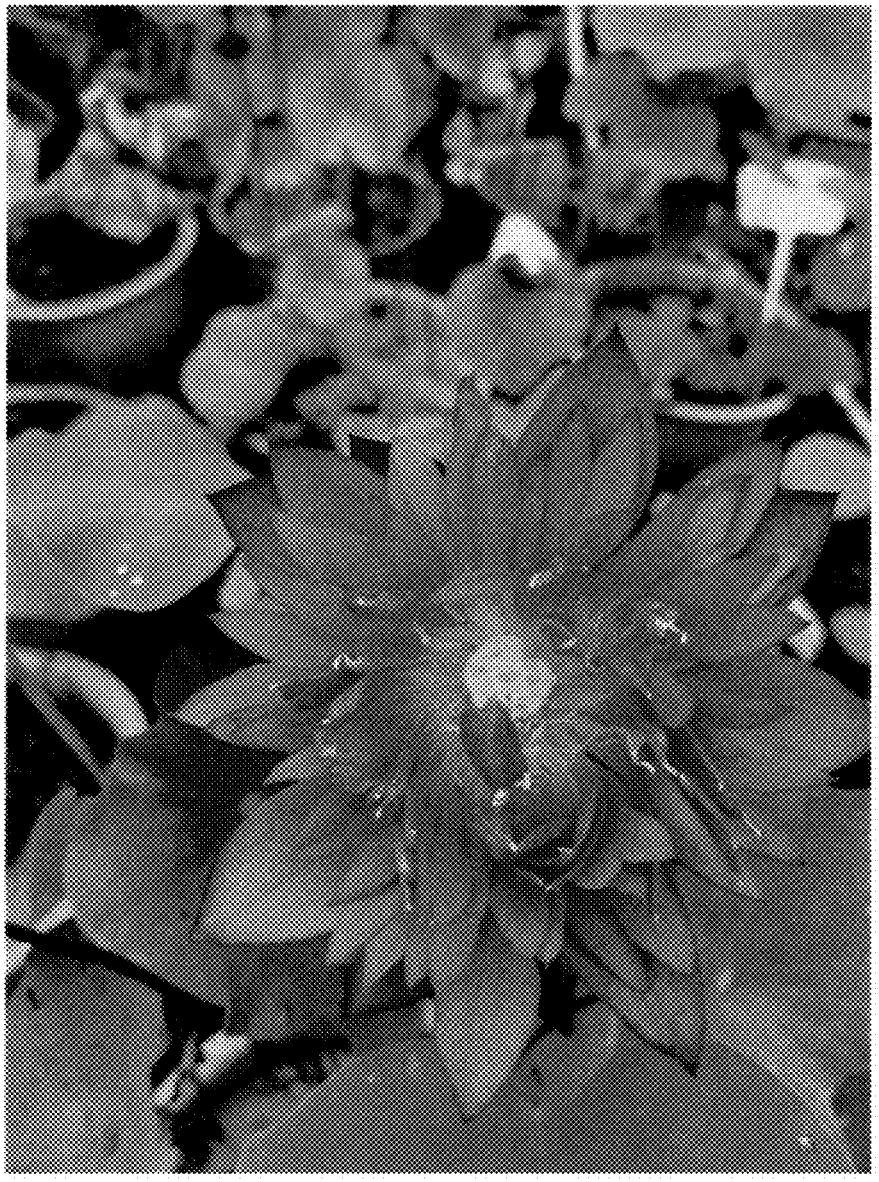
FIG. 1 illustrates in full color typical open flower of *Nelumbo* 'SCAU Star'.
Figure 2:
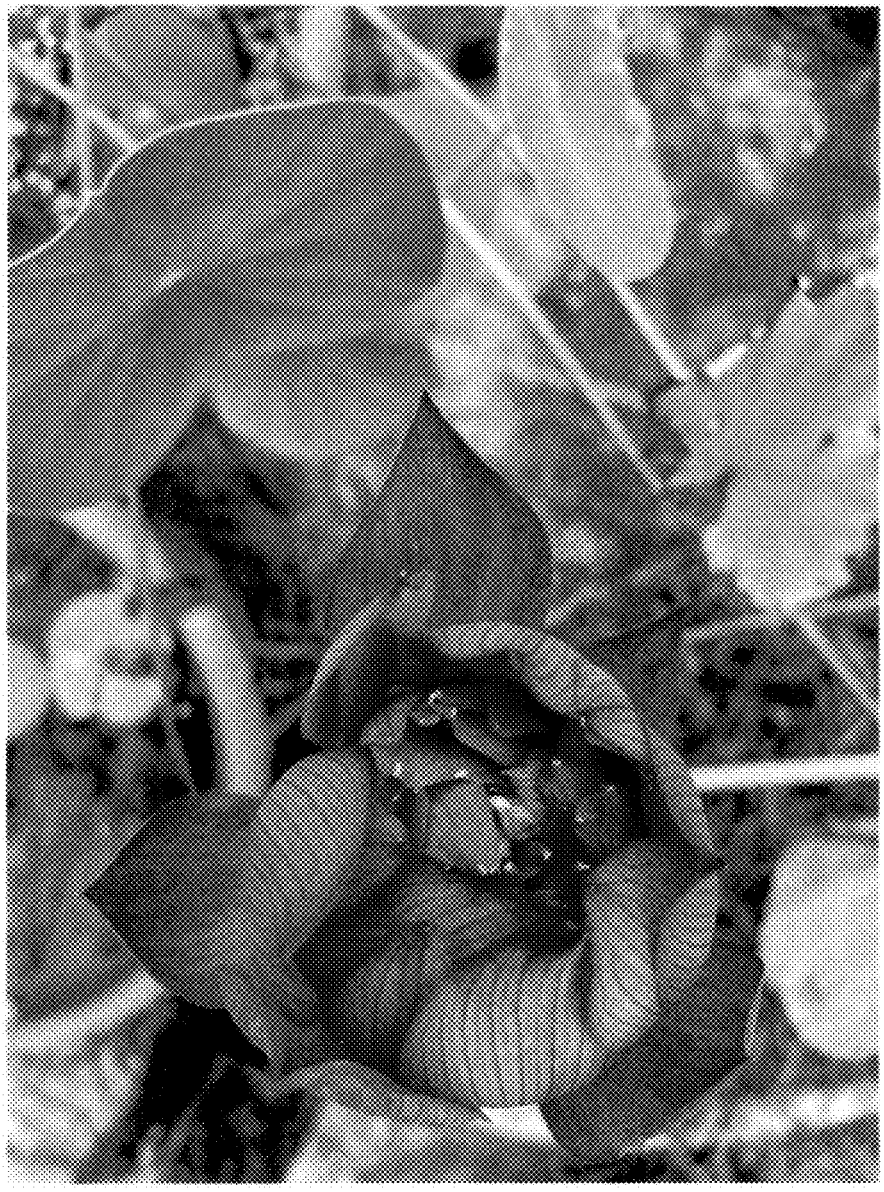
FIG. 2 illustrates in full color a typical unfurling flower of *Nelumbo* 'SCAU Star'.
Figure 3:
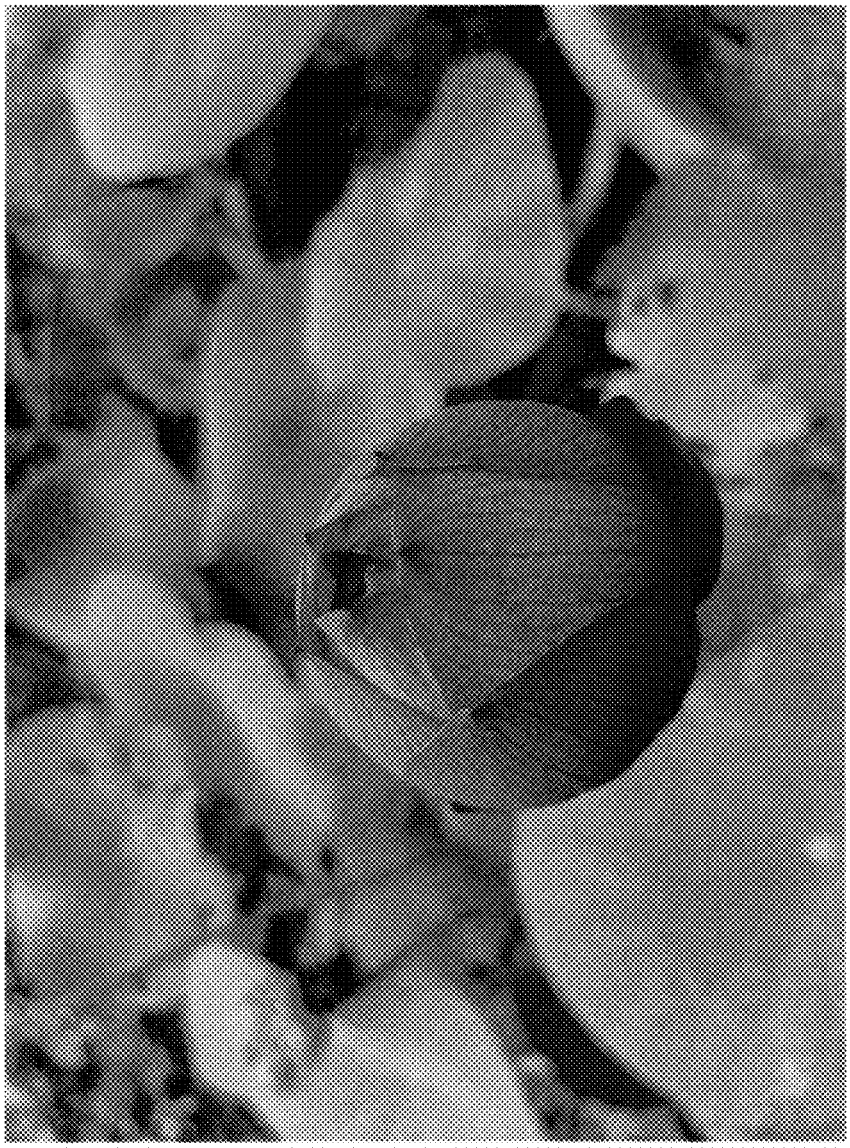
FIG. 3 illustrates in full color a typical flower bud of *Nelumbo* 'SCAU Star'.

In the following description, color references are made to The Royal Horticultural Society Colour Chart, 2015 (reprint 2019), except where general terms of ordinary dictionary significance are used. The following observations and measurements describe 'SCAU STAR' plants grown in an outdoor pond in Xuanwu district, Nanjing, China. The pond is approximately 4 meters in length, 90 cem in width and 25 cm deep. Average day temperature range was around 25° C. to 38° C.; average night temperature ranged around 20° C. to 30° C. No artificial light, photoperiodic treatments or chemical treatments were given to the plants. Natural light conditions were full sunlight. Measurements and numerical values represent averages of typical plant types. Measurements were taken during June to August of 2022.

Botanical classification: *Nelumbo nucifera* 'SCAU STAR'.

PROPAGATION

Type of propagation typically used: Root divisions.

Root description: Adventitious roots at the rhizome node. Moderately dense, moderately branching, medium thickness, fleshy texture. White in color, not accurately described with R.H.S. chart.

PLANT

Age of plant described: 1 year.

Container size of the plant described: In a pond of approximately 4 meters in length, 0.9 meters in width, and 25 cm in depth.

Growth habit: Heliophilous.

Height: Average 48 to 75 cm from water level to top of foliar plane: 65 to 88 cm from water level to top of floral plane.

Plant spread: Approximately 160 x 90 cm.

Growth rate: Moderate.

Branching habit: Sympodial, basal. No pinching required.

Primary branches/stems per plant: 5 to 10.

Secondary branches/stems per primary lateral branch: 3 to 5.

Lateral branch/stem length: 70 to 90 cm.

Lateral branch/stem diameter: 3 to 4 cm.

Internode length: 15 to 20 cm.

Stem:

*General description*.—Rhizome, nodose, cylindrical. Underground and underwater (in saturated soil or mud) stem.

*Aspect*.—Horizontal underground and underwater (in saturated soil or mud) growth.

*Strength*.—Weak.

*Color*.—Developing: Near Yellow-White 158B. At Internodes: Near Yellow-White 158B. Developed: Near Yellow 10D.

*Pubescence*.—None.

*Luster*.—Matte.

FOLIAGE

Leaf:

*Arrangement*.—Single leaf ranked, before and after flowering.

*Average length*.—Average 28 to 38 cm.

*Average width*.—24 to 33 cm.

*Shape of bladed*.—Orbicular, peltate.

*Apex*.—Dimple.

*Base*.—Leaf stalk attached to center of lower surface of orbicular leaf.

*Margin*.—Entire, slightly undulate.

*Texture of top surface*.—Smooth.

*Texture of bottom surface*.—Smooth, cancellate.

*Pubescence*.—None.

*Color*.—Young foliage upper side: RHS Yellow-Green 143B. Young foliage, under side: RHS Green 138C. Mature foliage upper side: RHS Green 138A. Mature foliage, under side: RHS Green 137A. Fall foliage upper side: RHS Greyed-Green 195B. Fall foliage, under side: RHS Greyed-Green 195C.

*Venation*.—Type: Reticulate. Venation color upper side: RHS Green 138D. Venation color under side: RHS Yellow-Green 144C.

Petiole:

*Length*.—Average range 47 cm to 63 cm.

*Diameter*.—Average range 0.5 cm to 0.9 cm.

*Color*.—Upper surface: RHS Yellow-Green 144B. Lower surface: RHS Yellow-Green 144B.

*Strength*.—Medium, stout.

*Texture*.—Glabrous.

*General description*.—Semi-woody, stiff, inside vertical hollows and latex.

*Luster*.—Weak.

*Other*.—Petioles have reddish-brown spines, most dense at base. Density of spines is about 20 per square cm.

FLOWER

Natural flowering season: Mid-June through late August.
Flower type and habit: Single, double-layered flowers. Upright. Freely flowering habit.
Flowers per plant: 11 to 15 per square meter.
Buds per plant: 7 to 9 per square meter.
Flower longevity on plant: 5 to 6 days. Self-cleaning.
Flower longevity as a cut flower: 3 to 4 days.
Flower size:
*Height*.—Approximately 14 to 16.2 cm.
*Width*.—Approximately 12 to 16 cm.
*Depth*.—5.5 to 8 cm.
Flower shape: Plated-shaped.
Bud:
*Shape*.—Broad ovate.
*Length*.—Approximately 6 to 7 cm.
*Diameter*.—Approximately 4.2 to 5.8 cm.
*Texture*.—Softly pubescent with rugose veins.
*Luster*.—None.
*Color*.—RHS Red 50A.
Petals:
*Arrangement*.—Whorled.
*Quantity*.—40 to 45 per flower.
*Number of whorls*.—Average 3.
*Fused*.—No.
*Margin*.—Entire.
*Shape*.—Obovate/oval.
*Apex*.—Acuminate.
*Base*.—Truncate.
*Texture*.—Papery, both surfaces.
*Rugosity*.—Smooth and weak.
*Luster*.—Weak, both sides.
*Petal length*.—6.7 to 8.2 cm.
*Petal width*.—2.5 to 5.5 cm.
*Color*.—When Opening: Upper Surface: RHS Red 52A. Under Surface: RHS Red 54A. Fully Opened: Upper Surface: RHS Red 52B. Veins 52B. Under Surface: RHS Red-Purple 58C. Veins N57C. Fading: Upper Surface: RHS Red 52B. Under Surface: RHS Red-Purple 58C.
Petaloids:
*Arrangement*.—Verticillate.
*Quantity*.—About 60 to 100 per flower.
*Number of whorls*.—2 to 4.
*Length*.—0.5 to 4.5 cm.
*Width*.—0.2 to 1.8 cm.
*Shape*.—Obovate-lanceolate.
*Margin*.—Entire.
*Apex*.—Apiculate.
*Base*.—Wedge.
*Texture*.—Papery, both surfaces.
*Rugosity*.—Smooth and weak.
*Luster*.—Weak, both sides.
*Color*.—When opening. Upper Surface: RHS Red 52A. Under Surface: RHS Red 54A Fully opened: Upper Surface: RHS Red 52B; venation 52B. Under Surface: RHS Red-Purple 58C. Veins N57C. Fading: Upper Surface: RHS Red 52B. Under Surface: RHS Red-Purple 58C.
Sepals:
*Quantity*.—4.
*Arrangement*.—Verticillate.
*Calyx shape*.—Oval.
*Fused*.—No.
*Number of whorls*.—2.
*Length*.—2.6 to 4.2 cm.
*Width*.—1.2 to 2.8 cm.
*Shape*.—Ovoid.
*Apex*.—Acuminate.
*Margin*.—Entire.
*Base*.—Truncate.
*Texture*.—Papery, both sides.
*Luster*.—Weak, both sides.
*Color*.—When Opening: Upper Surface: RHS Yellow-Green 144D. Under Surface: RHS Green 143C. Fully Opened: Upper Surface: RHS Greyed-Green 195A. Under Surface: RHS Greyed-Green 197B.
Fragrance: Moderate strength.
Peduncle:
*Length*.—54 to 82 cm.
*Diameter*.—0.5 to 0.8 cm.
*Strength*.—Medium, stout.
*Texture*.—Glabrous.
*General description*.—Semi-woody, stiff, inside vertical hollows and latex.
*Luster*.—Weak.
*Color*.—RHS Green 143C.

REPRODUCTIVE ORGANS

Stamens: (Androecium).
*Number*.—30 to 89.
*Filament length*.—6.5 to 9 mm.
*Filament color*.—Yellow 5C.
*Anther length*.—9 to 10 mm.
*Anther width*.—1 to 1.5 mm.
*Anther color*.—Yellow-Orange 17C.
*Anther shape*.—Bar.
*Pollen*.—Moderate.
*Pollen color*.—Yellow-Orange 22B.
Pistil: (Gynoecium).
*Number*.—24 to 33.
*Length*.—9 to 11 mm.
*Stigma*.—Shape: Circular. Color: Yellow-Orange 17C and Yellow 9A. Style Length: 1.5 to 2 mm. Stigma Diameter: 1 to 1.5 mm. Style Color: Yellow-Orange 17C. Ovary Color: Yellow 10D.

OTHER CHARACTERISTICS

Seeds: Seeds are aborted.
Fruit:
*Quantity*.—24 to 36 per plant.
*Length*.—3 to 3.8 cm.
*Diameter*.—4.2 to 6.5 cm.
*Texture*.—Smooth.
*Color*.—Near RHS Yellow-Green N144B, turning near Grey-Brown N199A then Black 202A.
*Taste*.—None.
*Days to ripen*.—21 to 40 days.
Root structures: Rhizomes.
*Shape*.—Cylindrical with nodes, expanded in winter.
*Length*.—80 to 110 cm.
*Diameter*.—0.5 to 3 cm.
*Texture*.—Fleshy.
*Color*.—Yellow-White 158C.
Temperature tolerance: Tolerates temperatures from approximately −10° C. to at least 40° C. High tolerance to rain; medium tolerance to wind. USDA hardiness zone 6A to 13B.

Disease/pest resistance: Medium resistance and susceptibility to normal diseases of *Nelumbo* observed. Medium resistance and susceptibility to normal pests of *Nelumbo* observed. The most common problem in Lotus is tuber deformation caused by the parasitic nematode *Hirschmanniella diversa* Sher and *H. imamur* Sher. Less commonly, leaf vein disease may also be seen, caused by *Nigrospora pyriformis*. Potential pests of Lotus include the waterlily aphid (*Rhopalosiphum nymphaeae*), red spider mite (*Tetranychus tumidus*) as well as thrips *Frankliniella schultzei* Trybom and *Scirtothrips dorsalis*.

What is claimed is:

1. A new and distinct cultivar of *Nelumbo* plant named 'SCAU STAR' as herein illustrated and described.

* * * * *